United States Patent
De Angelis et al.

(10) Patent No.: US 11,624,744 B2
(45) Date of Patent: Apr. 11, 2023

(54) METHOD AND DEVICE FOR RECORDING INTRACELLULAR ACTION POTENTIAL IN ELECTROGENIC CELLS

(71) Applicant: Fondazione Istituto Italiano di Tecnologia, Genoa (IT)

(72) Inventors: Francesco De Angelis, Genoa (IT); Michele Dipalo, Genoa (IT)

(*) Notice: Subject to any disclaimer, the term of this patent is extended or adjusted under 35 U.S.C. 154(b) by 124 days.

(21) Appl. No.: 15/733,161

(22) PCT Filed: Dec. 12, 2018

(86) PCT No.: PCT/IB2018/059936
§ 371 (c)(1),
(2) Date: Jun. 1, 2020

(87) PCT Pub. No.: WO2019/116257
PCT Pub. Date: Jun. 20, 2019

(65) Prior Publication Data
US 2020/0355670 A1  Nov. 12, 2020

(30) Foreign Application Priority Data
Dec. 13, 2017  (IT) .................. 102017000143666

(51) Int. Cl.
*G01N 33/483* (2006.01)
*G01N 1/44* (2006.01)

(52) U.S. Cl.
CPC .......... *G01N 33/4836* (2013.01); *G01N 1/44* (2013.01)

(58) Field of Classification Search
CPC ........ G01N 1/44; G01N 33/4836; G01N 3/00; G01N 1/00; G01N 5/00; G01N 7/00; G01N 9/00; G01N 11/00; G01N 13/00; G01N 15/00; G01N 17/00; G01N 19/00; G01N 21/00; G01N 22/00; G01N 23/00; G01N 24/00; G01N 25/00; G01N 27/00; G01N 29/00; G01N 30/00; G01N 31/00;
(Continued)

(56) References Cited

U.S. PATENT DOCUMENTS

| 2003/0111343 A1 | 6/2003 | Oka |
| 2011/0087315 A1* | 4/2011 | Richardson-Burns ... A61N 1/05 205/198 |
| 2017/0122938 A1 | 5/2017 | Naughton |

FOREIGN PATENT DOCUMENTS

| DE | 19827957 | 12/1999 |
| DE | 19827957 A1 * | 12/1999 ............ C12M 35/02 |
| WO | WO-2017115220 A1 * | 7/2017 ........... B23K 26/048 |

* cited by examiner

*Primary Examiner* — Lee E Rodak
*Assistant Examiner* — Brent J Andrews
(74) *Attorney, Agent, or Firm* — Themis Law (57) ABSTRACT

A method of recording intracellular action potentials in electrogenic cells through pores in membranes of cells formed by optoporation includes positioning a sample that includes the cells on a multi-electrode array; incubating or perfusing the sample; focusing a laser on the surface of the array electrodes, the surface contacting the sample; applying one or more laser pulses to one or more array electrodes to perform a localized breakdown of the membrane of the cells of the sample; and recording the intracellular action potentials. The surface of the electrodes is porous and has cavities and protrusions at the nanoscale level, and the electric field produced by the laser is localized and amplified to perform the localized breakdown of the membrane of the cells of the sample.

11 Claims, 4 Drawing Sheets

(58) Field of Classification Search
CPC ........ G01N 33/00; G01N 35/00; G01N 37/00; G01N 2201/00; G01N 2203/00; G01N 2223/00; G01N 2291/00; G01N 2333/00; G01N 2400/00; G01N 2405/00; G01N 2407/00; G01N 2410/00; G01N 2415/00; G01N 2430/00; G01N 2440/00; G01N 2446/00; G01N 2458/00; G01N 2469/00; G01N 2470/00; G01N 2474/00; G01N 2496/00; G01N 2500/00; G01N 2510/00; G01N 2520/00; G01N 2550/00; G01N 2560/00; G01N 2570/00; G01N 2600/00; G01N 2610/00; G01N 2650/00; G01N 2800/00; G01N 33/48728; C12M 35/02; C12M 1/3407

See application file for complete search history.

METHOD AND DEVICE FOR RECORDING INTRACELLULAR ACTION POTENTIAL IN ELECTROGENIC CELLS

The present invention relates to a method for recording intracellular action potentials in electrogenic cells through pores in the cellular membrane of cells formed by optoporation.

The method comprising the following steps:
a) positioning of a sample comprising said cells on a multi-electrode array;
b) incubation (110) or perfusion (111) of the sample;
e) focusing of a laser on the surface of the array electrodes, which surface contacts the sample;
f) application of one or more laser pulses to one or more array electrodes to perform a localized breakdown of the membrane of the cells of the sample;
g) recording of intracellular action potentials.

Methods of this type are currently known and used for recording action potentials in electrogenic cells such as neurons, cardiomyocytes, retina.

The use of multi-electrode arrays (MEA) for the recording of action potentials of large groups of cells has seen a great development in recent years.

Measurement of action potentials of a plurality of agglomerated cells in a large network may be extracellular or intracellular. In the first case the cell membrane being in electrical contact with a recording electrode is sufficient. In the second case it is instead necessary for the electrode to be in electrical contact with the cytoplasm of the cell. For this to happen, it is necessary to make pores in the cell membrane. At the state of the art there are two different methodologies that can be used for the creation of pores in the cell membrane: electroporation and optoporation.

The electroporation involves the application of short and intense high-voltage pulses such as to overcome the capacity of the cell membrane, allowing a temporary relaxation of the structure thereof and the formation of transient and reversible pores.

The optoporation, on the other hand, involves the use of high-intensity laser pulses capable of temporarily modifying the cell membrane for pore formation.

Both these methods are based on the use of three-dimensional (3D) nanostructures placed on the array electrodes, in order to create protrusions that can be found inside the pores when they are formed, so as to establish an electrical contact with the cytoplasm.

The currently used 3D nanostructures are generally characterized by a much greater height than the width. The height is typically in the range between 400 nanometers and 5 micrometers, while the width is typically in the range between 50 nanometers and 500 nanometers.

To date, the nanostructuring of the electrode with 3D structures with these proportions is a consolidated technique and makes it possible to produce almost any type of three-dimensional geometry.

However, all the techniques employed require specific and very expensive tools that are not usually the prerogative of the commercial semiconductor industry and are not easily scalable to a commercial level; as a result, the employment of 3D nanostructures on MEAs for intracellular recording has so far been limited to low-density passive MEA prototypes.

Regarding the recording of extracellular action potentials, all methods based on 3D nanostructures demonstrate worse performance than standard MEA electrodes.

Only recently 3D nanostructures on high-resolution CMOS active MEAs have been implemented for the recording of intracellular action potentials. This type of MEA can be used to perform an electroporation by means of electric pulse trains. For this purpose, the CMOS-MEA device includes, in addition to the recording amplification chain, a parallel stimulation circuit used to apply the electrical pulses.

However, this approach has some drawbacks. First, the silicon electronic circuit is significantly more complex due to the integration on the same electrode of the stimulation and recording circuits. This configuration results in having large elementary recording zones, or pixels, typically larger than $100 \times 100 \ \mu m^2$. This results in a lower resolution compared to other CMOS-MEA systems currently available on the market. Secondly, the electroporation process still requires the fabrication of 3D nanostructures for reliable performances. These characteristics result in a relatively low signal-to-noise ratio during extracellular recording before electroporation. Furthermore, electroporation can be applied only to the complete set of CMOS electrodes, without the possibility of selectively recognizing which cell or group of cells has been carried out.

3D nanostructures can affect cells in various ways, especially on cardiac cells that present mechanical contraction and may be affected by anchoring to 3D nanostructures; as a consequence, the recording of intracellular and extracellular potentials with 3D nanostructures is extremely invasive.

Furthermore, action potentials cannot be recorded during the application of electrical pulses, which are necessary to obtain intracellular recording. Cells receive a temporary trauma from the application of electrical pulses and consequently often stop generating action potentials for a while. For this reason, these known methods exhibit a high degree of invasiveness.

Recent studies have shown that plasmonic optoporation with 3D nanostructures on the electrode, particularly with 3D nanoantennas, can represent a very efficient alternative to electroporation for the production of pores in cells without damaging them. This method can be used for the intracellular recording of action potentials with passive MEAs. Despite the advantages of the opto-plasmonic approach, the known methods are nevertheless based on the plasmonic action of the 3D nanostructures. 3D nanostructures are very expensive to manufacture, must be fabricated with great precision to be able to resonate with laser light and are difficult to fabricate on high-density MEA, such as CMOS-MEA. Laser excitation of 3D nanostructures requires precise positioning and focusing of the laser on the tips of the nanostructures. This makes it very difficult to obtain reliable intracellular recording from a plurality of electrodes by scanning the laser on the surface of the device. The characteristics of the laser source must comply with specific requirements to efficiently excite the 3D plasmonic nanostructures and this limits the available laser sources that can be used. For all these reasons, this approach, like that of electroporation, has the disadvantage of providing complex and expensive manufacturing techniques, although it does not require electrical stimulation from the recording electrode.

Therefore, there is currently an unmet need for a method that allows the possibility of recording intracellular action potentials without 3D nanostructures nor complex electronic circuits.

The present invention aims to overcome the aforementioned drawbacks of the methods currently known, with a method as described at the beginning wherein said surface of the electrodes is porous, so that it presents cavities and protrusions at the nanoscale wherein the electric field produced by the laser is localized and amplified to perform said localized breakdown of the cell membrane of the sample.

The method therefore consists in the laser irradiation of the porous surface of the MEA electrodes. The membrane of the cell in contact with the porous surface is locally broken by the intense electromagnetic fields generated by the laser striking the porous surface. As a result, the inside of the cell comes contact with the electrode, which starts recording intracellular action potentials.

The morphology of the porous surface of the electrodes is fundamental for two reasons: (i) it increases the coupling between the cell and the electrode promoting a greater cell adhesion compared to that obtained by means of non-porous substrates, (ii) generates high intensity localized electromagnetic fields in the nano-gap of the porous surface during laser excitation. The first characteristic plays a fundamental role because it allows a very wide spatial adhesion between the cell membrane and the electrode, so strong and lasting that it can withstand even the subsequent membrane breaking process. Since the membrane remains attached to the electrode even after the pore opening induced locally by the laser, the pore itself is not in electrical contact with the extracellular environment. This in turn allows high-quality electrical potential measurements because it minimizes or completely eliminates leakage currents. The second reason (intensification of the electromagnetic field due to porosity) lies on several distinct optical characteristics. The first is that in the nano-gap of the porous material there can be localization and amplification phenomena in the electromagnetic field. The second is that the optical properties of porous metals are different from those of the respective starting materials. In particular, both the real and the imaginary part of the permittivity of a porous material may be lower than those of the starting material and the plasmonic response of the porous material may be more intense than in the starting metal. This generates a further and advantageous amplification of the electromagnetic field. Finally, as opposed to normal metals, the porous metal turns out to be dark in colour or behaves like an excellent broadband absorber. In summary, a porous metal has apparent optical advantages both in terms of coupling of the incident radiation and as a coupling efficiency with a wide spectral bandwidth, allowing a greater amplification and localization of the electromagnetic field.

All these advantages allow intracellular recording to be performed in a much cheaper and easier way compared to currently known methods. In fact, intracellular action potentials can be recorded without 3D nanostructures and without additional complex electronic circuits; these are necessary elements of all the other intracellular recording techniques that have been presented so far on MEA and CMOS-MEA. This difference is very important because it makes the recording process faster, more controllable and more reliable and less susceptible to changes between different MEAs.

In particular, the use of a porous surface is essential for obtaining the best recording performances both in extracellular and intracellular configuration.

Compared to other CMOS-MEA intracellular recording methods, this new approach offers greater spatial resolution thanks to the possibility of using smaller electrodes, a greater number of electrodes due to the simpler circuitry, and greater versatility thanks to the capacity of the single electrode poration. Furthermore, the new technique offers lower development and manufacturing costs due to the "already commercial" nature of the devices being used.

In this way, laser optoporation can be successfully applied to high-density commercial CMOS-MEAs, exploiting the porous surface of the electrodes, eliminating the need for stimulation circuits and 3D nanostructures. This approach allows to record intracellular action potentials of large cell groups using high-density commercial MEAs without any post-market modification of the devices.

The advantages of the method presented are many.

In the first instance, the method can be used with a large variety of passive or commercial active MEAs with electrodes that have a porous surface.

The method also does not require expensive and complex re-elaboration of devices such as in the case of manufacturing of 3D nanostructures, which are very expensive to produce and are not easy to integrate on commercial devices. Due to the difficulties in commercializing devices with 3D nanostructures, there are currently no commercial products that offer intracellular recording capability on MEA devices. On the contrary, this method can be relatively easy to market because it exploits cheaper devices that are already on the market. In principle, the method can be implemented by combining instruments and devices already marketed separately.

The method also allows to maintain an excellent SNR in extracellular mode.

The method also allows to get small pixels due to the absence of additional circuits. Intracellular recording can be obtained without additional electrical stimulation circuits on the CMOS-MEA. This allows the CMOS electrode to be optimized for recording performance. Thanks to the reduced pixel size, the spatial resolution of the recordings is greater. Furthermore, since laser excitation is completely independent from the MEA electrical recording system, the intracellular action potentials can be recorded from any culture or from individual cells that can be precisely identified. The selectivity is given by where the laser pulse is applied. The method therefore presents a high selectivity with respect to other methods applied on CMOS-MEA.

Finally, using the present method, the laser pulse application does not influence the electrical recording of the MEA, allowing continuous recording of the entire CMOS array before, during and after stimulation on selected electrodes. The recording of action potentials can in fact continue during the laser irradiation of the electrode. There are no interruptions in the recording of the entire MEA array. This feature offers the possibility to study the response of the cell culture to laser excitation in real time.

The positioning of the sample on the MEA can be performed by means of direct in vitro culture of the cells on the MEA or by placing on the MEA slices of biological samples of suitable thickness.

The focusing of the laser on the surface of the electrodes can be performed automatically or manually.

According to an exemplary embodiment, the surface of the electrodes is planar.

According to a further exemplary embodiment, the electrodes are, at least in the part comprising said surface, of metal, in particular of platinum or gold.

Gold offers an excellent optical coupling for laser excitation.

Platinum, however, is preferable because it is well established in the fields of cardiology and electrophysiology in general. The platinum surface has a configuration with a high nanoscale porosity, with a proportion of empty space in the volume of the porous material typically in the range between 30% and 70%. There are two distinct positive effects that derive directly from this surface morphology. On the one hand, the adhesion of the cells on the surface of the electrode is greatly improved, as has already been demonstrated in the literature. On the other hand, the surface presents nano-gaps and nano-tips wherein the electric field produced by the laser is localized and amplified. The combination of these two factors is responsible for the poration of the cell membrane and the subsequent intracellular recording mediated by laser excitation.

According to an improvement, the surface of the electrodes has a porosity developing in a thickness in the range between 100 and 500 nm. In particular, the surface of the electrode is developed with irregular protrusions for a thickness of about 400 nm.

In an exemplary embodiment, the surface of the electrodes has a material having empty spaces or pores with a size smaller than the wavelength of the incident light, preferably in the range between 10 nm and 300 nm. The proportion of empty space in the porous material volume is in the range between 30% and 70%.

In an embodiment a positioning step of the array is provided under an optical microscope, which optical microscope is provided with a first laser excitation optical path and a second optical image acquisition path.

The presence of the optical path allows to observe the cells on the electrodes and to correctly focus the laser used for the poration.

In a further embodiment a recording step of the extracellular action potentials from the whole array is provided.

This allows to obtain both extracellular and intracellular recording of action potentials.

According to a preferred exemplary embodiment, the surface of the electrodes does not have three-dimensional nanostructures specifically and neatly manufactured to create protrusions.

As specified above, this feature allows to avoid the manufacturing of 3D nanostructures that are very expensive to produce and are not easy to integrate on commercial devices. Furthermore, 3D nanostructures can affect cells in various ways, especially cardiac cells with mechanical contraction; as a consequence, the recording of intracellular and extracellular potentials with 3D nanostructures is extremely invasive.

Another object of the present invention is furthermore a device for recording intracellular action potentials in electrogenic cells, comprising a multi-electrode array (MEA) suitable to support a sample comprising said cells, a laser source, laser beam focusing means on the surface of the array electrodes, laser source driving means for the application of one or more laser pulses to one or more array electrodes to effect a localized breakdown of the membrane of the cells of the sample, cellular action potentials recording means detected by the electrodes, wherein said surface of the electrodes is porous.

In an exemplary embodiment, the surface of the electrodes is planar.

In an exemplary embodiment, the electrodes are made, at least in the part comprising said surface, of platinum or gold.

In an exemplary embodiment, the surface of the electrodes has a porosity that develops in a thickness in the range between 100 and 500 nm.

In an exemplary embodiment the laser source, the laser beam focusing means and the laser source driving means are part of an optical microscope, which optical microscope is provided with a first laser excitation optical path and a second optical image acquisition path.

In an exemplary embodiment, the surface of the electrodes does not have three-dimensional nanostructures specifically and neatly manufactured to create protrusions.

These and other features and advantages of the present invention will become clearer from the following description of some non-limiting exemplary embodiments illustrated in the attached drawings in which.

Figure 1:
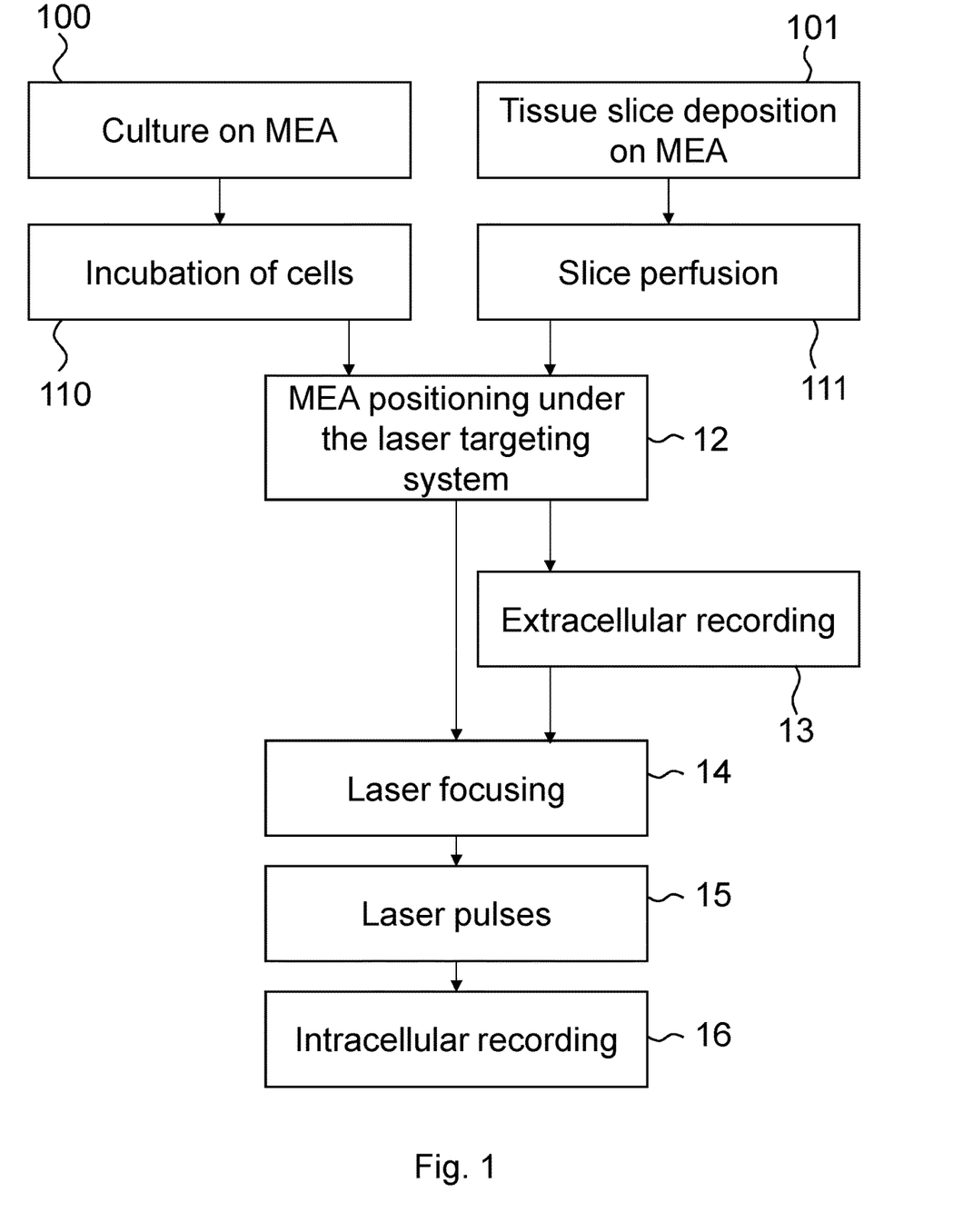
FIG. 1 shows a scheme of the method.

In FIG. 1 a block diagram of the action potentials recording method in electrogenic cells 4 object of the present invention is shown.

The cells 4 are grown in vitro 100 on a MEA device 2, for example a CMOS-MEA, and incubated 110.

Alternatively, slices of biological samples with a thickness in the range between 10 microns and 500 microns can be laid 101 on the MEA. Slices can be retinas, brain slices or slices of other tissues. In this case, perfusion 111 of the tissue slice is carried out during the experiment of extracellular and intracellular potentials recording.

For the laser excitation of the electrodes 20, the MEA device 2 is mounted 12 under an optical microscope provided with a first laser excitation optical path and a second optical image acquisition path.

Alternatively, a laser source 32 with a focusing lens is mounted above the MEA system. This configuration eliminates the need for a microscope and is ideal for industrial applications requiring automation.

Optionally, an extracellular recording 13 is performed
The laser is then focused 14 on the surface of the electrodes of the MEA device 2, which surface contacts with the cells 4. Focusing can be manual or automatic.

Laser pulses are applied 15 to one or more electrodes 20 of the MEA device 2 to perform cell optoporation.

Finally, the intracellular action potentials are recorded 16.

The recording procedure is performed on MEA devices 2 which have high surface porosity electrodes 20 at a nanoscale level.

Figure 2:
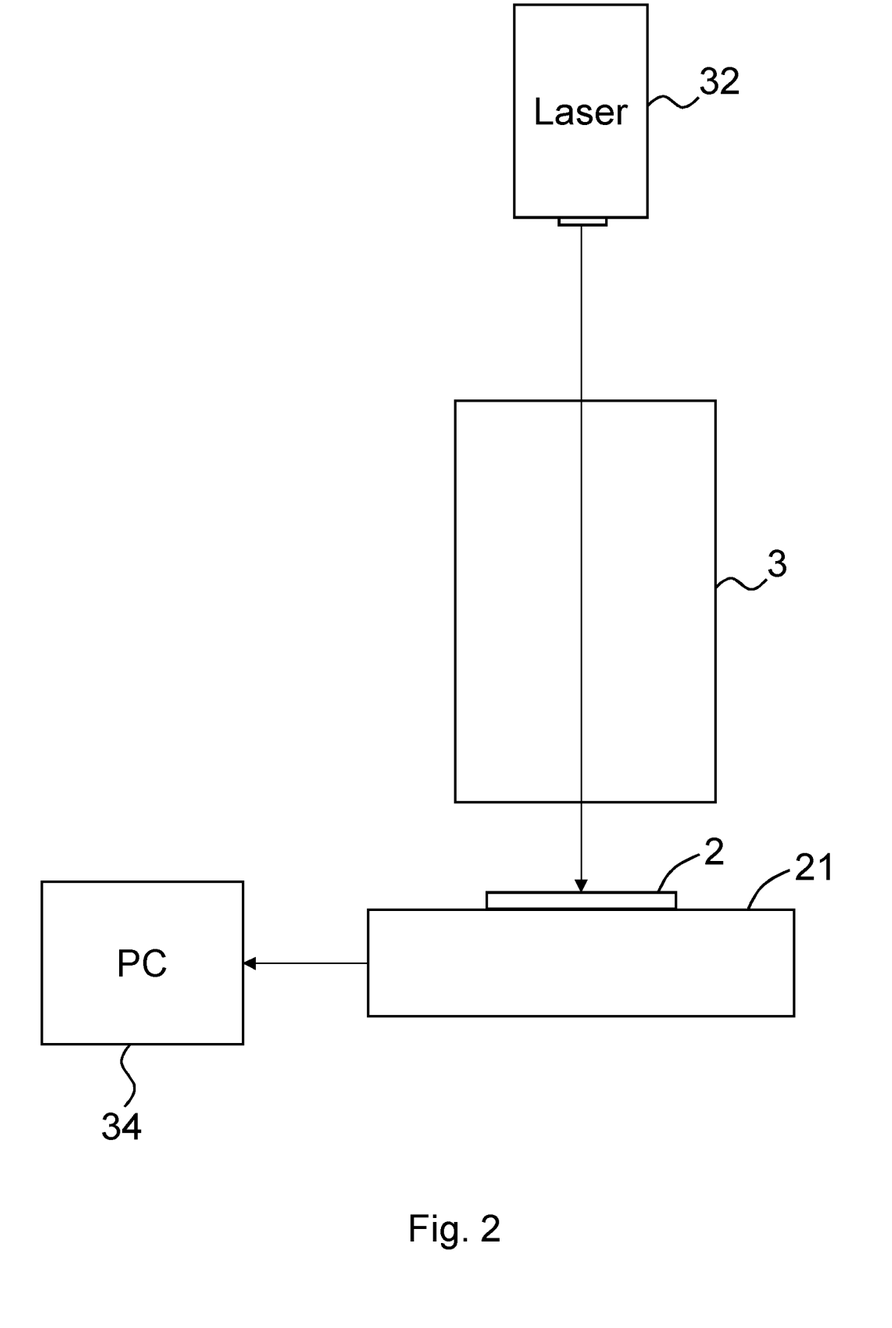
FIG. 2 shows a diagram of the device.

As shown in FIG. 2, the MEA device 2 is connected to cellular action potentials recording means detected by the electrodes 20, in particular a recording system 21.

Laser excitation is performed through an optical lens 3 connected to a laser source 32. The optical lens can optionally be inserted directly into the cellular medium. Laser excitation is performed using an 8 ps pulsed laser with a wavelength of 1064 nm.

Using a CCD/CMOS camera 33, the laser is focused automatically or manually on the porous surface of an electrode 20 of the MEA device 2. While the acquisition system 21 records the extracellular action potential from the complete MEA device 2, a laser pulse train is applied on one or more electrodes 20 to locally break the cell membrane adhering to these electrodes 20. Subsequently, these electrodes 20 record intracellular action potentials.

The laser can be directed manually and focused on a single electrode 20. Alternatively, a scanning system may be used to record intracellular action potentials from all the electrodes 20 of the MEA device 2.

In the example in FIG. 2, the device comprises a recording system MEA 21, a MEA device 2 provided with electrodes 20 with a porous surface, an optical system 3, a laser source 32, a computer 34 for acquiring data and focusing the laser on the electrodes 20.

An example of a MEA device 2 that can be used is a CMOS-MEA equipped with 4096 recording electrodes 20 with a size of 21×21 µm$^2$ and 21 µm of distance between the electrodes.

The system can be advantageously used for recording action potentials in cardiomyocytes. Considering the typical size of cardiomyocytes, which are larger than other electrogenic cells such as neurons, the aforementioned size of the electrode allows a single cell resolution recording. The electrodes are arranged in a 64×64 array covering an active area of 2.6×2.6 mm$^2$ of size.

In one exemplary embodiment of the method, laser excitation was performed using a 60× immersion lens inserted directly into the cell medium. Localized breakdown of the cell membrane by means of laser was performed using a pulsed laser at 8 ps and wavelength of 1064 nm.

Figure 3:
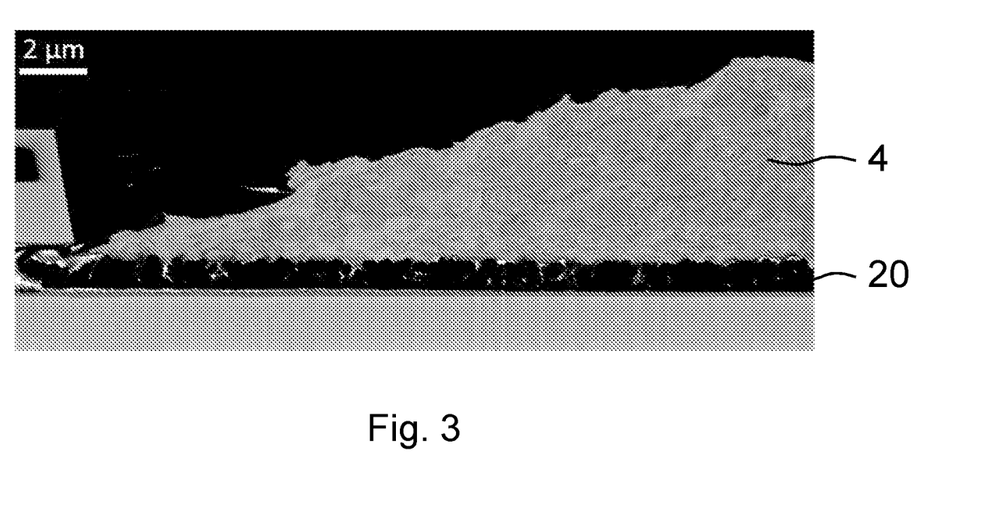
FIGS. 3 and 4 show two views of different detail of the surface of the electrodes with the cell in adhesion.
Figure 4:
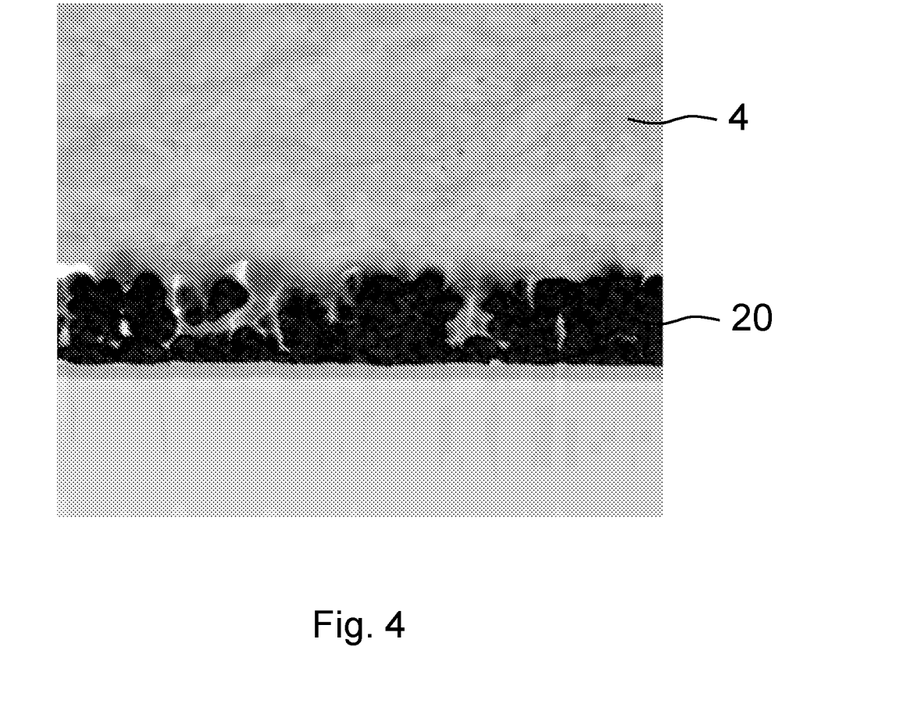

FIG. 3 and, more in detail, FIG. 4 show a cross-sectional view of the electrode 20 and of the electrogenic cell 4 in contact with the upper surface of the electrode 20. The electrode 20 is preferably of platinum. The platinum surface has a typical configuration of porous materials with a large nanoscale roughness. The cell after two days of in vitro culture is closely bound to the porous surface of the electrode 20: the figures show that there is a strong coupling between cells and platinum and that this close adhesion is continuous and extended over the whole contact surface between cell and electrode. It is also possible to observe the profile of the platinum surface layer, which develops with irregular protrusions for a thickness of about 400 nm.

Figure 5:
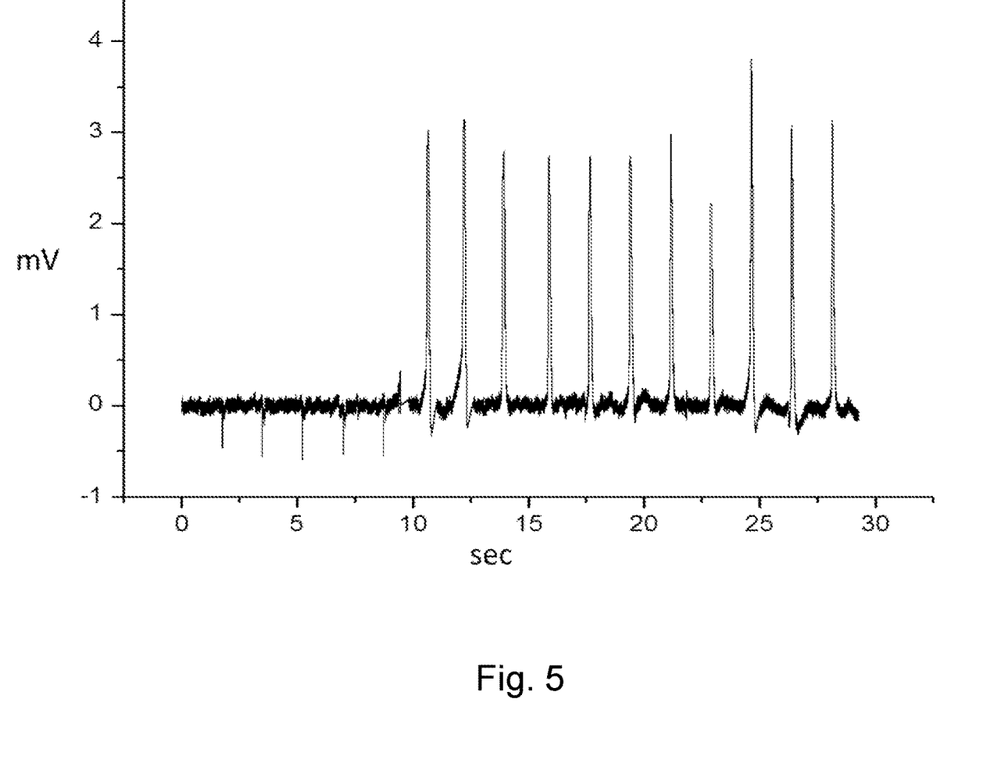
FIG. 5 shows a recording of action potentials.

FIG. 5 shows a diagram representing the cardiomyocyte action potentials recording from a CMOS-MEA electrode. On the left there are five extracellular action potentials recognizable by their predominant negative phase. After these five peaks the laser irradiation of the electrode is applied. The following action potentials have a completely different shape: the positive phase is now predominant, and the amplitude is much larger. The shape of the peaks after laser irradiation accurately reproduces that of the intracellular action potentials described in the literature.

The key role played by the platinum surface porosity due to the poration effect was evaluated with both experiments and simulations.

Intracellular potentials recording experiments were performed in parallel on CMOS-MEA with electrodes comprising porous or smooth platinum layers. The cells were placed on both types of devices and the recordings were performed in the same day. Laser excitation of electrodes with porous surface resulted in intracellular recordings using a laser power of a few mW (~0.5-2 mW). On the CMOS-MEA with smooth electrodes laser powers up to 30 mW were used without observing any change in the peaks, which maintained extracellular characteristics. Furthermore, laser excitation even at high power on planar electrodes did not produce any other effect on cells and their frequency of electrical activity. In addition to assessing the fundamental role played by the platinum porous surface in the process of laser-mediated intracellular recording, this experiment also has a second important result. In fact, it confirms that, without the influence of the porous platinum layer, the direct irradiation of cells with the fast-pulsed laser does not have negative effects on cellular activity even at remarkably high-power levels. This is also due to the characteristics of the laser used in the experiments, in particular the ultra-short laser pulses and the extremely low work cycle (0.064% ON-OFF).

Parallelly to the experiments, simulations were performed to evaluate the effects of laser irradiation on smooth and porous platinum. The simulations demonstrate that the electric field reaches considerably higher values in the case of porous platinum compared to the case of the smooth platinum surface, where the field is evenly distributed at the laser focusing point.

The instantaneous thermal behaviour during a single 8 picoseconds laser pulse was also simulated; the results for the porous surface and for laser powers in the range between 0.5 and 5 mW show that the surface temperature increases only by about 5-10° C. More importantly, the temperature drops very quickly to the equilibrium value before it starts the next laser pulse, thus explaining the negligible heat accumulation during the complete laser pulse train. The temperature gradient is confined to a time window of about 10 nanoseconds, which is well below the typical reaction time of the TRP channels.

The invention claimed is:

1. A method of recording intracellular action potentials in electrogenic cells through pores in cell membranes of cells formed by optoporation, comprising the following steps:
   positioning a sample comprising said cells on a multi-electrode array;
   incubating or perfusing the sample;
   focusing a laser on a surface of array electrodes of the multi-electrode array, said surface contacting the sample;
   applying one or more laser pulses to one or more of the array electrodes to perform a localized breakdown of a membrane of the cells of the sample; and
   recording intracellular action potentials;
   wherein said surface of the array electrodes is porous, so that said surface has cavities and protrusions at a nanoscale level; and
   wherein an electric field produced by the laser is localized in said cavities and protrusions and amplified to perform said localized breakdown of the membrane of the cells of the sample.

2. The method according to claim 1, wherein the array electrodes are made, at least in a part comprising said surface, of platinum or gold.

3. The method according to claim 1, wherein the surface of the array electrodes has a porosity, which develops in a thickness between 100 and 500 nm.

4. The method according to claim 1, wherein the surface of the array electrodes has empty spaces or pores with a size smaller than a wavelength of incident light.

5. The method according to claim 1, further comprising a step of positioning the multi-electrode array under an optical microscope, said optical microscope being provided with a first laser excitation optical path and a second optical image acquisition path.

6. The method according to claim 1, further comprising a step of recording extracellular action potentials from the entire multi-electrode array.

7. The method according to claim 1, wherein the surface of the array electrodes does not have three-dimensional nanostructures specifically and neatly manufactured to create protrusions.

8. A device configured to record intracellular action potentials in electrogenic cells, comprising:
   a multi-electrode array configured to support a sample comprising said cells;
   a laser source;
   a laser beam focusing device adapted to focus a laser beam on a surface of the electrodes of the multi-electrode array;

a laser source driving system adapted to apply one or more laser pulses to one or more electrodes of the multi-electrode array to carry out a localized breakdown of a membrane of the cells of the sample; and a system adapted to record cellular action potentials detected by the electrodes, wherein said surface of the electrodes is porous with cavities and protrusions thereon, and wherein an electric field produced by the laser beam is localized in said cavities and protrusions and amplified to perform said localized breakdown of the membrane of the cells of the sample.

9. The device according to claim 8, wherein the electrodes are, at least in a part comprising said surface, of platinum or gold.

10. The device according to claim 8, wherein the surface of the electrodes has a porosity that develops in a thickness between 100 and 500 nm.

11. The device according to claim 8, wherein the laser source, the laser beam focusing device, and the laser source driving system are part of an optical microscope, said optical microscope being provided with a first laser excitation optical path and a second image acquisition optical path.

* * * * *